(12) United States Patent
Hershenhorn et al.

(10) Patent No.: US 8,785,721 B2
(45) Date of Patent: Jul. 22, 2014

(54) PEST RESISTANT PLANT

(75) Inventors: Joseph Hershenhorn, Shimshit (IL); Evgenia Dor, Afula (IL); Yoram Kapulnik, Carmey Yossef (IL); Samdar Goldar Weininger, Rishon-Lezion (IL); Bruria Ben Dor, Rishon-Lezion (IL)

(73) Assignee: State of Israel, Ministry of Agriculture, Beit Dagan (IL)

( * ) Notice: Subject to any disclaimer, the term of this patent is extended or adjusted under 35 U.S.C. 154(b) by 312 days.

(21) Appl. No.: 13/128,286

(22) PCT Filed: Nov. 18, 2009

(86) PCT No.: PCT/IL2009/001090
§ 371 (c)(1),
(2), (4) Date: Jul. 6, 2011

(87) PCT Pub. No.: WO2010/058399
PCT Pub. Date: May 27, 2010

(65) Prior Publication Data
US 2011/0258732 A1    Oct. 20, 2011

(30) Foreign Application Priority Data

Nov. 18, 2008 (EP) .................................... 08169310
May 5, 2009 (EP) .................................... 09159445

(51) Int. Cl.
*A01H 5/08* (2006.01)
*A01H 5/00* (2006.01)
*A01H 5/10* (2006.01)

(52) U.S. Cl.
USPC ......... 800/265; 800/301; 800/317.4; 800/298

(58) Field of Classification Search
None
See application file for complete search history.

(56) References Cited

U.S. PATENT DOCUMENTS 5,897,866 A   4/1999   Bombardelli et al.

FOREIGN PATENT DOCUMENTS

| EP | 1103579 A1 | 5/2001 |
|----|------------|--------|
| WO | 03090554 A1 | 11/2003 |
| WO | WO 2006/098626 A2 | 9/2006 |

OTHER PUBLICATIONS

Kasrawi et al, 1989, HortScience, 5:822-824.*
Lopez-Raez et al, 2008, J. Argic. Food Chem., 56: 6326-6332.*
Levin et al, 2003, Theor. Appl. Genet., 106:454-460.*
Brummel et al, 2001, Plant Mol. Bio., 47:311-340.*
Xianquan et al, 2005, J. Medicinal Food, 8:413-422.*
Hershenhorn et al., Workshop Parasitic Plant Management in Sustainable Agriculture, Final Meeting of COST849, Nov. 23-24, 2006, ITQB, Oeiras-Lisbon, Portugal, p. 35.
Vijay et al., Rhizosphere 2, International Conference Montpellier, France, Aug. 26-31, 2007, p. 55.
El-Halmouch et al., Crop Protection, 2006, 25, pp. 501-507.
Qasem et al., Euphytica, 1995, 81, 1, pp. 109-114.
Aly Radi et al., Plant Cell Reports, 2006, 25, 4, pp. 297-303.
Andeyev et al., TGC Report, 2005, 55, pp. 46-47.
Lopez-Raez et al., Journal of Agricultural and Food Chemistry, 2008, 56, 15, pp. 6326-6332.
Kostov et al., Bulgarian Journal of Agricultural Science, 2007, 13, pp. 505-513.
Aly et al., Workshop Parasitic Plant Management in Sustainable Agriculture, Final Meeting of COST849, Nov. 23-24, 2006, ITQB Oeiras-Lisbon, Portugal, p. 21.
Andeev et al., Soviet Agricultural Sciences, 1978, 1, pp. 14-16.
Kasrawi et al., Hortscience, 1989, 24, 5, pp. 822-824.
Rispail et al., The New Phytologist, 2007, 173, 4, pp. 703-712.
Evgenia et al., Euphytica, 2010, 171, 3, pp. 371-380.
Dor et al., Workshop Parasitic Plant Management in Sustainable Agriculture, Final Meeting of COST849, Nov. 23-24, 2006, ITQB Oeiras-Lisbon, Portugal, 2006, p. 32.

* cited by examiner

*Primary Examiner* — David H Kruse
*Assistant Examiner* — Jason Deveau Rosen
(74) *Attorney, Agent, or Firm* — The Law Office of Michael E. Kondoudis (57) ABSTRACT

The present invention relates to tomato plants that are resistant to pathogenic plants of the Orobanchaceae family, to methods for producing said plants and to the use thereof. The invention further relates to a method of controlling parasitic plants of the Orobanchaceae family, particularly *O. aegyptiaca*, in tomato crops and for securing tomato fruit production.

19 Claims, 2 Drawing Sheets

PEST RESISTANT PLANT

CROSS REFERENCE TO RELATED APPLICATIONS

This application is a §371 of International Patent Application No. PCT/IL2009/001090, filed Nov. 18, 2009, which claims priority to European Patent Application Nos. 08169310.3, filed Nov. 18, 2008 and 09159445.7, filed May 5, 2009, which are incorporated herein by reference.

The present invention relates to tomato plants that are resistant to pathogenic plants of the Orobanchaceae family, to methods for producing said plants, and to the use thereof.

Parasitic weeds cause enormous yield losses in agriculture, economically threatening many countries, including Israel, Egypt, Jordan, Tunisia, Turkey and many others. A large part of Israel's agriculture is based on crops which are hosts to parasites of the Orobanchaceae or broomrape family, such as processing and fresh tomatoes, sunflowers, and more. Parasites of the Orobanchaceae family cause heavy damage to agriculture and threaten to ruin the processing tomato industry in Israel.

Infected crops can be heavily damaged even before *Orobanche* inflorescences emerge above soil. *Orobanche* spp. are holoparasites that lack chlorophyll and depend intimately on their host for survival. They suck water and nutrients through the roots of their host. *Orobanche cumana* Wallr. parasitizes sunflower in Spain, Turkey as well as in Eastern Europe around the Black Sea (Joel et al., 2007) *O. cernua* is closely related to *Orobanche cumana* but parasitizes a wider range of hosts, mainly *Solanaceous* species. *O. ramosa* is widely spread in Southern Europe and the Mediterranean region and was introduced to regions of South Africa, USA and Central America (Musselman, 1994). *O. aegyptiaca* and its closely related species, *O. ramosa*, parasitizes a wide range of hosts such as tomato, potato, eggplant, tobacco, cucurbits, crucifers, sunflower and some other vegetables such as carrot, celery, parsnip and lettuce (Press and Graves, 1995). *O. crenata* is a widespread parasite of legumes all around the Mediterranean (Press and Graves, 1995).

Control of the *Orobanche* parasites is particularly difficult and the means currently available are expensive and potentially hazardous for the environment. Development of plant lines that contain a genetic-based resistance to parasites of the broomrape family offers an efficient long term solution for controlling these parasites. This method is preferable over existing methods presently used for controlling Orobanchaceae parasites, such as chemical and biological methods, because it is easy to use, and does not pose a threat to human health or the environment.

This is not only an advantage for freshly produced tomatoes and processed tomatoes intended for human consumption, but also for the further processing of tomato extracts for extracting carotenoids such as lycopene.

To date, tomato plants resistant to parasites of the Orobanchaceae family are not available, and classical breeding methods have not been successful in producing resistant lines.

Therefore, there is a need for cost-efficient, easy to use and environmentally friendly methods for protecting plants, particularly tomato plants, from infestation with parasitic *Orobanche* species.

Within the scope of the present invention this need is satisfied by providing a tomato plant that contains in its genome a genetic determinant that is controlling the expression of a resistance to a parasitic plant of the Orobanchaceae family, particularly to *O. aegyptiaca*.

In one embodiment, the present invention provides a tomato plant exhibiting a resistance to a parasitic plant of the Orobanchaceae family, particularly to *O. aegyptiaca*, wherein said resistance is controlled by a genetic determinant, particularly a heritable genetic determinant.

In one embodiment, the present invention provides a tomato plant exhibiting a resistance to a parasitic plant of the Orobanchaceae family, particularly to *O. aegyptiaca*, wherein said resistance is controlled by a genetic determinant, and wherein said genetic determinant is freely transmissible between different tomato plants or lines. The *Orobanche* resistant trait can thus be readily transferred by conventional breeding from deposited seed material, particularly from deposited seed material of tomato line ORT-10, deposited with NCIMB under accession number NCIMB 41586 or tomato lines derivable therefrom, to any tomato plant or line of interest, including commercial elite tomato lines or varieties.

The invention further provides a tomato plant exhibiting a resistance to a parasitic plant of the Orobanchaceae family, particularly to *O. aegyptiaca*, wherein said resistance is controlled by a genetic determinant, which shows a Mendelian inheritance and is freely transmissible between different tomato plants or lines.

In one embodiment, a tomato plant according to the invention is provided, wherein said genetic determinant controlling the *Orobanche* resistance is represented by at least one gene which shows a recessive inheritance, particularly a recessive Mendelian inheritance.

In one embodiment, a tomato plant according to the invention and as described herein is provided, wherein said genetic determinant controls production and/or secretion of a chemical compound that is capable of stimulating germination of seeds of a parasitic plant of the Orobanchaceae family, particularly of seeds of *O. aegyptiaca*.

In one embodiment, a tomato plant according to the invention is provided, wherein production and/or secretion of said germination stimulating chemical compound is inhibited.

The invention further relates to a tomato plant according to the invention and as described herein, which provides a root exudate which upon application to seeds of a parasitic plant of the Orobanchaceae family, particularly of *O. aegyptiaca*, in a seed germination assay results in a germination rate of not more than 5%, particularly of not more than 4%, particularly of not more than 3%, particularly of not more than 2%, particularly of not more than 1%, particularly of not more than 0.5%, but especially of 0%.

The invention further relates to a tomato plant according to the invention and as described herein, which provides a root extract upon extraction of root tissue with an extracting agent such as, for example, ethyl acetate, which upon application to seeds of a parasitic plant of the Orobanchaceae family, particularly of *O. aegyptiaca*, in a seed germination assay results in a germination rate of not more than 5%, particularly of not more than 4%, particularly of not more than 3%, particularly of not more than 2%, particularly of not more than 1%, particularly of not more than 0.5%, but especially of 0%.

In one embodiment, the above seeds germination rates are obtainable by applying a seed germination assay comprising
preconditioning of *Orobanche* seeds to be tested in an incubator at a temperature of at least 24° C., particularly of at least 26° C., particularly of at least 28° C., for a period of at least 4 days, particularly of at least 6 days, wherein the seeds may be kept on moist filter paper, particularly on glass fiber filter paper discs (9 mm) which were kept on a moist Whatman filter paper;

transferring, at the seventh day, the seeds to a supporting medium such as fresh Petri plate lined with moist filter paper rings on its wall and allowing the seeds to dry for at least 15 minutes, particularly for at least 20 minutes, under suitable conditions such as those provided in a sterile hood cabinet;

adding root exudates to each disc at a volume of at least 20 µl, particularly of at least 40 µl;

keeping the discs in the incubator for at least 4 days, particularly for at least 6 days; and calculating the percentage of seed germination.

A synthetic germination stimulant such as GR 24 (5 ppm) may be used as a positive control and water as a negative control.

In one embodiment, the above seeds germination rates are obtainable by applying a seed germination assay as disclosed in Example 6.

The tomato plant according to the invention and as described herein can be obtained from a donor plant comprising a genetic determinant directing and/or controlling expression of the *Orobanche* resistance phenotype through introgression of said genetic determinant into a recipient plant, which is susceptible to infestations with the *Orobanche* parasite, particularly to infestations of *O. aegyptiaca*.

In one embodiment, tomato line ORT-10, deposited with NCIMB under accession number NCIMB 41586 or a tomato line derivable therefrom, can be used as such a donor plant for the *Orobanche* resistance trait. The trait can be readily transferred from the deposited seed material to any tomato plant or line of interest, including a commercial elite line or variety, by conventional breeding.

In one embodiment, the invention relates to tomato plant line ORT-10, deposited with NCIMB under accession number NCIMB 41586.

In one embodiment, the Orobanchaceae parasite is *O. aegyptiaca*.

The invention further provides a tomato plant exhibiting a resistance to a parasite of the genus Orobanchaceae, wherein said resistance is controlled by a genetic determinant, which shows a Mendelian inheritance and is freely transmissible between different tomato plants or lines, wherein the progenitor of said genetic determinant is native to the tomato plant and now mutated, particularly by chemical/physical means such as application of a mutagenizing agent or "Fast Neutron" treatment, to direct expression of the *Orobanche* resistance phenotype in said tomato plant.

In one embodiment, the genetic determinant of the *Orobanche* resistant plant according to the invention and as described herein is represented by at least one gene, particularly by one gene, which shows a recessive, Mendelian inheritance.

In one embodiment of the invention, a tomato plant is provided exhibiting a resistance to a parasite of the Orobanchaceae family, wherein said resistance becomes manifest in the behavior of the plant towards an infestation with an *Orobanche* parasite, in that the resistant plant stays essentially unaffected and only shows a decrease of less than 5%, particularly of less than 4%, particularly of less than 3%, particularly of less than 2%, particularly of less than 1%, but especially of 0% in one or more of the parameters selected from the group consisting of plant height, wet and dry weight of branches, wet and dry weight of the root system without the parasite, wet and dry weight of the foliage, wet and dry weight of the infested root including the broomrape parasite.

In one embodiment of the invention, an *Orobanche* resistant tomato plant is provided as described herein, wherein the wet weight of the Orobanchaceae parasite growing on said resistant plant is about 10 times less than that of a parasite growing on a sensitive plant.

In another embodiment of the invention, an *Orobanche* resistant tomato plant is provided as described herein, wherein said plant is resistant, particularly fully resistant, to a parasite of the Orobanchaceae family, particularly to *O. aegyptiaca*.

In still another embodiment of the invention, an *Orobanche* resistant tomato plant is provided as described herein, wherein said plant is resistant, particularly fully resistant, to a parasite of the Orobanchaceae family, particularly to *O. aegyptiaca* at a parasite seed concentration of less than 10 ppm, particularly of less than 15 ppm, particularly of less than 20 ppm, particularly of less than 30 ppm, particularly of less than 40 ppm, but especially of less than 50 ppm.

In another embodiment of the invention, an *Orobanche* resistant tomato plant is provided as described herein, wherein said plant is resistant to at least one parasite selected from the group consisting of *O. aegyptiaca, O. cernua, O. crenata* and *O. ramosa*.

In one embodiment of the invention, an *Orobanche* resistant tomato plant is provided as described herein, wherein said tomato plant inhibits production and/or secretion of a chemical compound that is capable of stimulating the germination of *Orobanche* seeds.

The plant according to the invention and as described herein before may be an inbred, a hybrid and/or a male sterile.

In one embodiment, said tomato plant according to the invention and as described herein is male sterile.

In one embodiment, the *Orobanche* resistant plant according to the invention and as described herein before contains a "resistant" trait, which is obtainable from tomato line ORT-10, deposited with NCIMB under accession number NCIMB 41586.

In one embodiment, the tomato plant according to the invention and as described herein is a lycopene enriched tomato plant, particularly a tomato plant with a lycopene content in the range of between 40 mg/kg and 200 mg/kg, or more.

In one embodiment, the invention relates to plant material obtainable from an *Orobanche* resistant plant according to the invention and as described herein before including, but without being limited thereto, leaves, stems, roots, flowers or flower parts, fruits, pollen, egg cells, zygotes, seeds, cuttings, cell or tissue cultures, or any other part or product of the plant which still exhibits the resistance phenotype according to the invention.

The invention further relates to plant parts obtainable from an *Orobanche* resistant plant according to the invention and as described herein before including, but without being limited thereto, plant seed, plant organs such as, for example, a root, stem, leaf, flower bud, or embryo, etc, ovules, pollen microspores, plant cells, plant tissue, plant cells cultures such as, for example, protoplasts, cell culture cells, cells in plant tissues, pollen, pollen tubes, ovules, embryo sacs, zygotes and embryos at various stages of development, etc; which still exhibits the *Orobanche* resistance phenotype according to the invention, particularly when grown into a plant.

In one embodiment, the present invention provides tomato fruits suitable of being used as fresh produce, as fresh cut produce, or for processing such as, for example, canning.

The invention further relates to a method of producing an *Orobanche* resistant tomato plant comprising the steps of introgressing from a donor plant comprising a genetic determinant directing and/or controlling expression of the *Orobanche* resistance phenotype into a recipient plant, which lacks a functional genetic determinant directing and/or controlling expression of the *Orobanche* resistance phenotype and is thus susceptible to infestations with the *Orobanche* parasite, particularly to infestations of *O. aegyptiaca*, by (a) crossing said donor plant with said recipient plant to obtain a progeny plant exhibiting the *Orobanche* resistance, (b) screening for and selecting from the progeny plants a plant exhibiting an *Orobanche* resistant phenotype and, optionally, harvesting the resultant progeny seed.

In one embodiment, tomato line ORT-10, deposited with NCIMB under accession number NCIMB 41586 is used as the donor plant for the *Orobanche* resistance trait, or a tomato line derivable from said ORT-10 line.

In one embodiment, the present invention provides a method of producing an *Orobanche* resistant tomato plant according to the present invention and as described herein comprising grafting
  a) the scion of an *Orobanche* resistant tomato plant according to the invention and as described herein on the rootstock of a sensitive tomato plant; or
  b) the rootstock of an *Orobanche* resistant tomato plant according to the invention and as described herein on the scion of a sensitive tomato plant.

The invention also relates to an *Orobanche* resistant tomato plant produced by any of the methods described herein.

In one embodiment of the invention, a method is provided for securing tomato fruit production to a commercially relevant extent in a geographical area with a high incidence of *Orobanche* parasites comprising growing an *Orobanche* resistant tomato plant according to the invention and as described herein in said geographical area.

In one embodiment of the invention, a method is provided for controlling parasitic plants of the Orobanchaceae family, particularly *O. aegyptiaca*, in tomato crops, particularly in tomato crops grown in the field or protected cultivation, comprising obtaining an *Orobanche* resistant tomato plant according to the invention and as described herein and growing said plant in a field contaminated with seeds of the *Orobanche* parasite.

The invention further relates to a tomato plant exhibiting a resistance to a parasitic plant of the genus *Orobanche*, which plant is obtainable by a method according to the invention and as described herein.

The invention also relates to a fruit of a tomato plant according to the invention and as described herein, particularly to a processed fruit.

Also comprised by the invention is the use of seed deposited under accession number NCIMB 41586 for the production of an *Orobanche* resistant tomato plant.

In another embodiment of the invention relates to the use of an *Orobanche* resistant tomato plant according to the invention and as described herein for the manufacture of vegetal extract or concentrate, particularly a vegetal extract or concentrate that is enriched in carotenoid and/or phytosterol.

In still another embodiment of the invention, the *Orobanche* resistant tomato plant according to the invention and as described herein is used for the extraction of at least one carotenoid, particularly a carotenoid selected from the group consisting of lycopene, lutein, phytoene, phytofluene, neurosporene, alpha-carotene, beta-carotene, γ-carotene, ζ-carotene, astaxanthine, and zeaxanthin; particularly from lycopene, lutein, alpha-caroten, beta-carotene, astaxanthine or zeaxanthin or precursors thereof.

The invention further relates to a method of producing carotenoids, particularly carotenoids chosen from lycopene, lutein, phytoene, phytofluene, neurosporene, alpha-carotene, beta-carotene, γ-carotene, ζ-carotene, astaxanthine, and zeaxanthin, particularly from lycopene, lutein, alpha-caroten, beta-carotene, astaxanthine or zeaxanthin or precursors thereof comprising the following steps:
  a) providing orobanche resistant tomato plant according to the invention and as described herein;
  b) growing the tomato plant to full maturity of the tomato fruit;
  c) harvesting the fruits, and
  d) extracting said carotenoids from the fruit.

DEFINITIONS

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

As used herein, the term "trait" refers to a characteristic or phenotype, e.g., mature fruit color or a disease or pathogen resistance such as *Orobanche* resistance. A trait may be inherited in a dominant or recessive manner, or in a partial or incomplete-dominant manner. A trait may be monogenic (i.e. determined by a single locus) or polygenic (i.e. determined by more than one locus) or may also result from the mutual interaction among genes or interaction of one or more genes with the environment. A dominant trait results in a complete phenotypic manifestation at heterozygous or homozygous state; a recessive trait manifests itself only when present at homozygous state.

The term "*Orobanche* Resistance", "resistant against Orobanchaceae", or similar terms as used herein refers to a tomato plant that highly restrict the growth and development of the specified pest or pathogen under normal pest or pathogen pressure when compared to susceptible counterparts. These plants may, however, exhibit some symptoms or damage under heavy pest or pathogen pressure. The level of resistance against a parasitic plant of the Orobanchaceae family, particularly against a plant pathogen of *O. aegyptiaca*, exhibited by a given plant can be scored, for example, by means of a standardized seed germination assay such as that described in Example 6 herein below.

In particular, an "*Orobanche* resistant plant" is understood for the purpose of the present invention to refer to a plant that shows essentially no induction of seed germination in parasitic plants of the Orobanchaceae family, particularly in parasitic plants of *O. aegyptiaca*, if grown in the presence of said seed. The seed germination rate of a parasitic plant of the Orobanchaceae family, particularly of a parasitic plant of *O.*

*aegyptiaca*, can be determined in a standardized seed germination assay such as that described in Example 6 herein below.

By "essentially no induction" a germination rate determined in such a standardized seed germination assay is understood that is not higher than 5%, particularly not higher than 4%, particularly not higher than 3%, particularly not higher than 2%, particularly of not higher than 1%, particularly not higher than 0.5%, but especially 0%. In consequence, the term "resistant" as used herein means a resistance in the classical sense (no susceptibility) but is also meant to include a tolerance (i.e., a significantly reduced susceptibility as defined above).

The seeds germination rates referred to above can be obtained by applying a seed germination assay comprising
- preconditioning of *Orobanche* seeds to be tested in an incubator at a temperature of at least 24°, particularly of at least 26°, particularly of at least 28° C., for a period of at least 4 days, particularly of at least 6 days, wherein the seeds may be kept on moist filter paper, particularly on glass fiber filter paper discs (9 mm) which were kept on a moist Whatman filter paper;
- transferring, at the seventh day, the seeds to a supporting medium such as fresh Petri plate lined with moist filter paper rings on its wall and allowing said seeds to dry for at least 15 minutes, particularly for at least 20 minutes under suitable conditions such as those provided in a sterile hood cabinet;
- adding root exudates to each disc at a volume of at least 20 µl, particularly of at least 40 µl;
- keeping the discs in the incubator for at least 4 days, particularly for at least 6 days; and
- calculating the percentage of seed germination.

A synthetic germination stimulant such as GR 24 (5 ppm) may be used as a positive control and water as a negative control.

In particular, a seed germination assay may be applied as disclosed in Example 6.

As used herein, the phrase "susceptibility" refers to the inability of a plant to adequately restrict the growth and development of a specified pest or pathogen, particularly of a parasitic plant of the Orobanchaceae family, particularly a plant of *O. aegyptiaca*.

In particular, a "susceptible tomato plant" refers to a plant that shows a substantial induction of seed germination in parasitic plants of the Orobanchaceae family, particularly in parasitic plants of *O. aegyptiaca*, if grown in the presence of said seed.

By "substantial induction" a germination rate determined in a standardized seed germination assay, particularly a seed germination assay as described in Example 6, is understood that is higher than 60%, particularly higher than 65%, particularly higher than 70%, particularly higher than 75%, particularly higher than 80%, particularly higher than 85%, but especially 90% and more.

As used herein, the term "allele(s)" means any of one or more alternative forms or variant forms of various genetic units identical or associated with different forms of a gene or of any kind of identifiable genetic element, all of which alleles relate to at least one trait or characteristic. In a diploid cell, the two alleles of a given gene occupy corresponding loci on a pair of homologous chromosomes and are, therefore, alternative in inheritance.

Such alternative or variant forms may be the result of single nucleotide polymorphisms, insertions, inversions, translocations or deletions, or the consequence of gene regulation caused by, for example, by chemical or structural modification, transcription regulation or post-translational modification/regulation.

In some instances it may be more accurate to refer to "haplotype" (i.e. a haplotype is a combination of alleles at several or multiple linked loci (on the same chromosome) that are transmitted together) instead of "allele", however, in those instances, the term "allele" should be understood to comprise the term "haplotype". Alleles are considered identical when they express a similar phenotype, but in some cases it can happen that different alleles also express a similar phenotype. Differences in sequence are possible but of less importance as long as they do not influence phenotype.

An allele associated with a quantitative trait may comprise alternative or variant forms of various genetic units including those that are identical or associated with a single gene or multiple genes or their products or even a gene disrupting or controlled by a genetic factor contributing to the phenotype represented by said QTL.

A "genetic determinant" is defined herein as a nucleotide sequence, preferably a DNA sequence that may comprise sequences with various genomic functions such as genes and regulatory elements regions. Genetic determinant may also refer to a nucleotide construct and may be comprised in a vector. Alternatively, a genetic determinant may be transferred from one plant to another by chromosomal recombination after crossing said plants. A genetic determinant may in principle comprise genetic material originating from one or more species.

In particular, genetic determinant as used herein refers to a single gene or multiple genes, a QTL or a haplotype, that determines or controls expression of the *Orobanche* resistance phenotype in a tomato plant.

A "gene" is defined herein as a hereditary unit consisting of a sequence of DNA that occupies a specific location on a chromosome and that contains the genetic instruction for a particular characteristics or trait in an organism.

A "locus" is defined herein as the position on a genetic map that a given gene or any other genetic element or factor contributing to a trait occupies on a chromosome of a given species.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

The terms "chromosome" is meant to include, and thus used herein synonymously with, the terms "linkage group" and/or "chromosome equivalent of linkage group", respectively.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes. Homozygosity is defined as absence of segregation after selfing of an individual plant or, if crossed, absence of segregation in F1.

As used herein, the terms "hybrid", "hybrid plant," and "hybrid progeny" refers to an individual produced from genetically different or unlike parents (e.g., a genetically heterozygous or mostly heterozygous individual) (Rieger et al., 1968).

As used herein, the phrase "single cross $F_1$ hybrid" refers to an $F_1$ hybrid produced from a cross between two inbred lines.

As used herein, the phrase "inbred line" refers to a genetically homozygous or nearly homozygous population. An inbred line, for example, can be derived through several cycles of brother/sister breedings or of selfing. In some embodiments, inbred lines breed true for one or more phenotypic traits of interest. An "inbred", "inbred individual", or "inbred progeny" is an individual sampled from an inbred line.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the $F_1$, the $F_2$, or any subsequent generation.

As used herein, the terms "introgression", "introgressed" and "introgressing" refer to the process whereby genes, a QTL or haplotype of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

"Polymorphism" is understood within the scope of the invention to refer to the presence in a population of two or more different forms of a gene, genetic marker, or inherited trait or a gene product obtainable, for example, through alternative splicing, DNA methylation, etc.

"Selective breeding" is understood within the scope of the invention to refer to a program of breeding that uses plants that possess or display desirable traits as parents.

"Tester" plant is understood within the scope of the invention to refer to a plant of the genus *Solanum* used to characterize genetically a trait in a plant to be tested. Typically, the plant to be tested is crossed with a "tester" plant and the segregation ratio of the trait in the progeny of the cross is scored.

As used herein, the term "population" means a genetically homogeneous or heterogeneous collection of plants sharing a common genetic derivation.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "tomato" or "*Lycopersicon*" is meant to include any species, variety, cultivar, or population of the *Lycopersicon* genus, particularly *L. esculentum*. now newly designated as genus *Solanum* and species *Solanum lycopersicum*, respectively.

A "cultivated *Lycopersicon* or *Solanum*" plant is understood within the scope of the invention to refer to a plant that is no longer in the natural state but has been developed by human care and for human use and/or consumption.

As used herein, the term "breeding", and grammatical variants thereof, refer to any process that generates a progeny individual. Breedings can be sexual or asexual, or any combination thereof. Exemplary non-limiting types of breedings include crossings, selfings, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

"Backcrossing" is understood within the scope of the invention to refer to a process in which a hybrid progeny is repeatedly crossed back to one of the parents. Different recurrent parents may be used in subsequent backcrosses.

"Processed tomato plant" is understood within the scope of the invention to refer to tomatoes that are processed into (1) peeled products for, for example, canning, and/or (2) concentrated products such as puree, sauce and paste.

The following description is provided, alongside all chapters of the present invention, so as to enable any person skilled in the art to make use of said invention. Various modifications, however, will remain apparent to those skilled in the art, since the generic principles of the present invention have been defined specifically to provide an *Orobanche* resistant tomato plant with unique characteristics as set forth below.

Within the scope of the present invention a tomato plant is provided that contains in its genome a stable, heritable genetic determinant that is responsible for the expression of a resistance to a parasite of the genus Orobanchaceae, particularly to *O. aegyptiaca*. This genetic determinant can be obtained from line ORT-10, which was developed from the commercial tomato variety M-82 through application of a "Fast Neutron" mutagenic technique, or from any line derivable from said ORT-10 line which still contains the genetic determinant responsible for the expression of a resistance to a parasite of the Orobanchaceae family, particularly to *O. aegyptiaca*.

Tomato line ORT-10 was deposited with NCIMB Aberdeen AB21 9YA, Scotland, UK on 22 Oct. 2008 under accession number NCIMB 41586.

Based on genetic experiments it could be shown that the resistance to parasites of the Orobanchaceae family is controlled by a genetic determinant, which is heritable and can be freely transmitted between different tomato species and lines such as to induce expression of the resistance phenotype in those tomato species and lines, which lack the resistance phenotype and are, therefore, susceptible to infestations with parasites of the Orobanchaceae family. Plants expressing the resistance trait can then be identified phenotypically.

In one embodiment of the invention, the genetic determinant controlling the *Orobanche* resistance trait is introgressed into a tomato line which has one more of the following traits that are useful for transporting and processing of tomatoes. This set of traits is designated "Processing Quality Factors" (or PQFs).

1. Holding ability of the fruit on the plant, i.e., firm fruit walls and thick skin, no decay of older fruits, no germination of seeds in the older fruits, no breakdown of sugars inside the older fruits, and no fermentation within the older fruit.
2. Firmness of the fruits to withstand mechanical harvesting and transportation as well as storage under open sky conditions at 38° C. without significant breakdown and disease development.
3. Firmness of the fruits to withstand high pressure steam (e.g., 15-30 psi at 105°-120° C.) and/or application of chemicals (e.g., 11-19% NaOH at 85°-99° C.) to peel the skin off the fruits.
4. Firmness of the fruits to withstand high pressure steam for cooking as whole tomatoes.
5. Firmness of the fruits to withstand cutting to make diced tomato products.
6. Firmness of the sliced and diced tomato products to withstand cooking with high pressure steam.

In a specific embodiment, the genetic determinant controlling the *Orobanche* resistance trait is introgressed into a tomato line which has one more of the PQF traits identified above and/or a high content in carotenoids, particularly in carotenoids selected from the group consisting of lycopene, lutein, phytoene, phytofluene, neurosporene, alpha-carotene, beta-carotene, γ-carotene, ζ-carotene, astaxanthine, and zeaxanthin, particularly from lycopene, lutein, alpha-caroten, beta-carotene, astaxanthine or zeaxanthin, to obtain progeny plants which exhibit a desirable phenotype, i.e. a plant which exhibits resistance to *Orobanche* pathogen and a high content of carotenoids and/or at least one of the above PQFs.

In one embodiment, the genetic determinant controlling the *Orobanche* resistance trait is introgressed into a tomato line which has high content of lycopene, particularly in the range of between 40 mg/kg and 200 mg/kg, or more, to obtain progeny plants which exhibit both desirable phenotypes, the *Orobanche* resistance and the high lycopene content.

The resistance phenotype as exhibited by mutant tomato line ORT-10 can be characterized by means of morphological parameters including plant height, wet and dry weight of the root system, wet and dry weight of the foliage, dry and wet weight of the infested root+the broomrape parasite, the resistance spectrum to different parasites of the genus Orobanchaceae, and the potential of root exudates and extracts for stimulating germination of *Orobanche* seeds.

In one aspect of the invention, the *Orobanche* resistance was characterized to determine the extent of the resistance offered by the trait obtainable from the ORT-10 resistant line, by examining different measurable parameters, which are indicative for the resistance including plant height, wet and dry weight of the root system, wet and dry weight of the foliage, dry and wet weight of the infested root+the broomrape parasite. The experiments were usually run for a period of about 8 weeks. Beginning 3 weeks after commencement of the trial start, and each week until the conclusion, plants were sampled and the soil washed off from the plants in order to visually inspect and compare the root system of the resistant and the sensitive plant lines, respectively. Plant height, wet and dry weight of the root system, wet and dry weight of the foliage, dry and wet weight of the root including the broomrape parasite were recorded.

While the germination rate is significantly different for parasites exposed to resistant or sensitive tomato lines, up until the 4$^{th}$ week after planting, no difference can be observed in the foliage height, dry and wet weight of the foliage, wet and dry weight of the root system of the resistant and the sensitive tomato plant and dry and wet weight of the tested broomrape parasites in either the resistant or the sensitive plants, independent of whether the 2 lines were grown in soil infected or uninfected with the Orobanchaceae parasite. This is still the period in which the parasite is in its early stages of development and has not succeeded yet to damage the host in a significant way.

Beginning with week 5 after planting, until the end of the experiment, a number of differences can be observed in the condition of sensitive and resistant plants if grown in soil infected with the pathogen, which are indicative of the presence of a resistance mechanism in the resistant line.

In sensitive plants a decrease in all of the aforementioned parameters can be observed due to the attachments of the Orobanchaceae parasite to the host roots, establishing of connections with the vascular system of the host plant by means of mechanical and enzymatic mechanisms, sucking out of nutrients and photosynthates and disabling or interfering with the host's development processes. It also produces tubercles, spiders and inflorescences, etc. In contrast to plants susceptible to *Orobanche* parasites, the resistant plants stay mostly unaffected and show only a slight decrease in some of said parameters.

In line with these observations, it could be shown that again beginning with week 5 and until the end of the experiment, there was a significant rise in wet weight of the Orobanchaceae parasite growing on sensitive plants, which was about 10 times higher than that observable in resistant plants.

Further, a decrease in the root and foliage wet and dry weight of the sensitive plants grown in soil infested with *O. aegyptiaca* in comparison to uninfected plants could be observed, which is also indicative of the damage caused by the parasite.

In contrast, almost no difference could be observed in resistant plants between the wet and dry weight of plants grown on infected or uninfected soil. It could further be shown that the resistant plants display lasting characteristics of resistance to the Orobanchaceae parasites.

These observations are in line with histological findings, which show that histological reactions of the resistant host plant at or close to the penetration site of the Orobanchaceae parasite limit the water and nutrient transport to the parasite. Due to these changes, disorganization of Orobanchaceae cells occur, causing necrosis of tissue around the area of penetration of the host plant (Dörr et al., 1974; Goldwasser et al., 1997). In sunflower parasitized by *O. cumana*, parasite death occurs at later stages of parasitism, i.e., at the stage of tubercle formation or at the stage of spider production, a phenomenon which explains the very small number of spiders and flowers that can be observed in sunflower broomrape parasitizing roots of resistant sunflower plants (Eizenberg et al., 2004). Note that the resistant sunflower 'Amber' gave identical results with 3 species of Orobanchaceae, (*O. ramosa, O. cumana*, and *O. aegyptiaca*) and the germination and death of the parasite after successful germination, attachment, penetration and establishment in the host root tissue.

In, the hypersensitive response, the cells under attack immediately lose membrane permeability, turgor is reduced, cellular transpiration increases at a tremendous rate and the cells under attack die immediately. The attacking parasite stays in the necrotic region and does not spread. This defense mechanism was described by Alonso, 1998; Serghini et al., 2001. Jorrin et al., 1999; Wegman et al., 1989, 1991 showed the correlation between release of Phytoalexins by the host (scopoletin) and resistance to Orobanchaceae, which lead to the conclusion that phytoalexins are involved in resistance of sunflower to *O. cernua*.

It was shown in *Orobanche* resistant sunflowers that both sensitive and resistant sunflower lines stimulate the germination of sunflower seeds and that the resistance mechanism becomes activated only at later stages of the parasite development (Jorrin et al., 1999, Labrousse et al., 2001, Eizenberg et al., 2003).

It was further known form the prior art that the germination process of Orobanchaceae seeds requires a host secreted chemical stimulant/s, but not the host itself. The Orobanchaceae seed will not germinate without such chemical stimulant/s.

For the resistance observed in tomato plants, essentially two options were considered. The resistance of the tomato plant line could be caused by an inhibition of stimulant secretion, which is either due to a blockage of the chemical synthesis or the secretion of the stimulant, or to the production of an inhibitory substance by the host plant, which causes inactivation of the stimulant.

Another possibility is based on observations reported by Alonso, 1998; Serghini et al., 2001, which explain resistance in terms of phytotoxic substances. Release of these substances during the different stages of the parasite development such as germination, attachment to the tomato roots, and penetration into the host vascular system, may cause necrosis and death of the parasite. In order to determine which of the above mechanisms is responsible for the resistance observed in tomato line ORT-10 the following experiments were carried out.

Resistant and sensitive plants were co-cultivated in the same growing pots in different designs. In one of said designs only ORT-10 plants were grown and no inflorescences of the Orobanchaceae parasite could be observed. In an alternative design a resistant plant was grown surrounded by 4 sensitive plants. In this case, a high number of inflorescences could be observed similar to a design where only sensitive plants were grown in a single pot. If indeed a toxic substance had been released by the resistant plant, the number of inflorescences should have been significantly reduced as compared to the arrangement only comprising sensitive plants.

It could therefore be reasonably concluded that the resistance may be caused by a complete blockage or a reduction of the synthesis and/or secretion of the stimulating compound necessary for germination of the *Orobanche* seeds or by the release of a compound which inhibits said stimulating compound once it has been produced by the host plant and/or released to the environment.

To test this hypothesis the severity of pathogen infestation with *O. aegyptiaca* after treatment of the *Orobanche* seeds with a synthetic germination stimulating compound (GR24) was examined.

In control studies, where the *Orobanche* pathogen was grown in the absence of host plants, no germination of seeds was observed. This demonstrates that under the experimental conditions, no spontaneous germination occurs in *O. aegyptiaca*.

The percentage of germination of *Orobanche* seeds placed in the vicinity of the root system of the sensitive tomato line in a paper envelope design as described in the Examples, was high with values between 76% and 85%, regardless of the presence of the synthetic stimulant GR 24. The number of tubercles attached per 1 cm root length was about 2. The percentage of germination of *Orobanche* seeds without the presence of the synthetic stimulant GR 24, grown in the vicinity of the roots of resistant line ORT 10 was negligible and reached not more than 0.7%, and only 0.1 tubercles were found attached to 1 cm of root length. Germination of *Orobanche* seeds pre-treated with GR 24 in the vicinity of ORT 10 roots reached 85% with one tubercle attached per 1 cm of root length.

The above results suggest that the resistance is caused by a reduced or an entirely lacking release of stimulating compounds from the resistant plant roots, but not by release of a substance which inhibits or destroys the stimulant activity. Otherwise, one would not have observed any germination or very low germination of *O. aegyptiaca*, after application of the synthetic stimulant.

This hypothesis is further supported by the results of a seed germination assay, wherein root exudate and root extract obtained from sensitive and resistant plant lines was tested for its germination stimulating potential towards seeds of a parasitic plant of the genus Orobanchaceae, particularly seeds of *O. aegyptiaca*.

In one aspect of the invention, root exudate was obtained from sensitive and resistant plants grown in the greenhouse under standard conditions ((25/20° C. day/night). Exudate may be collected from the root system by immersion in distilled water, particularly double distilled water and used in a seed germination assay. Root extract may be collected from the root system by grounding the roots in liquid nitrogen followed by extraction with ethyl acetate. After centrifugation, the pellet is resuspended in distilled water, particularly double distilled water and used in a seed germination assay.

It could be demonstrated that neither the root exudate nor the root extract upon administration to *Orobanche* seeds exhibited any germination stimulating activity.

The tomato plants according to the present invention and as described herein can be used in commercial tomato seed production. Commercial tomatoes are generally hybrids produced from the cross of two parental lines (inbreds). The development of hybrids requires, in general, the development of homozygous inbred lines, the crossing of these lines, and the evaluation of the crosses.

Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes and characteristics. The new inbreds are crossed with other inbred lines and the hybrids from these crosses are evaluated to determine which of those have commercial potential. Plant breeding and hybrid development are expensive and labour and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population in order to generate an established breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1 to F2; F3 to F4; F4 to F5, etc. A single cross hybrid results from the cross of two inbred lines, each of which has a genotype that complements the genotype of the other. The hybrid progeny of the first generation is designated F1. In the development of commercial hybrids only the F1 hybrid plants are sought. Preferred F1 hybrids are more vigorous than their inbred parents. This hybrid performance (hybrid vigor or heterosis), can be manifested in many polygenic traits, including increased vegetative growth and increased yield. Tomato plants can be easily cross-pollinated. A trait is also readily transferred from one tomato plant to another plant, including tomato plants of different types using conventional breeding techniques, for example to further obtain commercial lines. The introgression of a trait into the elite line is for example achieved by recurrent selection breeding, for example by backcrossing. In this case, the elite line (recurrent parent) is first crossed to a donor inbred (the non-recurrent parent) that carries the trait, particularly the "*Orobanche* resistance" trait according to the present invention. The progeny of this cross is then mated back to the recurrent parent followed by selection in the resultant progeny for the trait. After three, preferably four, more preferably five or more generations of backcrosses with the recurrent parent with selection for the trait, particularly the "*Orobanche* resistance" trait according to the present invention, the progeny is heterozygous for the locus harbouring the resistance, but is like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376, incorporated herein by reference). Selection for the trait is carried out after each cross. Male sterility is available in tomato. In particular genetic male sterility may be used in commercial lines. e.g., sweet tomato lines (see for example Alexander Kilchevsky and Michail Dobrodkin, Acta Physiologiae Plantarum Volume 22, Number 3/September 2000).

In another aspect of the present invention, tomato fruits are obtained from an *Orobanche* resistant tomato plant according to the invention and as described herein by growing said tomato plant to full maturity of the tomato fruit; and harvesting the fruits. The fruits can then be used for further processing into (1) peeled and/or (2) concentrated products.

(1) Peeling for canned tomatoes may be performed by treating the tomatoes with either steam or lye (NaOH). For steam peeling, tomatoes are scalded in live steam long enough to loosen the skin. For an efficient tomato peeling operation, it is essential that the skin be completely loosened.

Chemical peeling of tomatoes may be accomplished by a 11-19% solution of Caustic soda or sodium hydroxide, also called lye. A high temperature (85-99° C.) solution of caustic soda dissolves the waxy cuticular layer of the skin of tomatoes and quickly disrupts outer tissues of the fruit while leaving the inner flesh untouched.

Only tomatoes with very firm fruit walls can be subjected to high pressure steam and/or caustic soda for peeling. Tomatoes with softer tissues do not remain intact and tend to lose significant weight during the process. In addition, a significant amount of tomatoes are made sliced and diced.

(2) More than 65% red tomatoes are processed into concentrated products such as puree, sauce and paste. Tomato juice is made by grinding whole tomatoes in high temperature juice to maintain pectins and other chemical constituents of tomatoes that contribute to viscosity of juice. Purees range from light to heavy with soluble solids ranging from 8-10% for light and 11.3-15% for heavy.

Paste is generally 32% soluble solids. Juice contains 4-5.5% soluble solids. Only the tomatoes having pH of 4.3 and below (measured in fresh or cooked juice) at full maturity are suitable for processing.

Ketchup, Mexican salsa, pasta sauce, pizza sauce, barbecue sauce, cocktail sauce, tomato based salad dressings and other products are manufactured from paste. Color and flavor retention are absolutely essential during the concentration process starting with the juice at 5% soluble solids and reaching paste at 32% soluble solids. Reconstituted products from paste need to have tomato taste and color for consumer acceptance.

Tomato paste or extract may not only be used for direct human consumption, but is the starting material for extraction of valuable metabolites that are present in the tomato fruit such as carotenoids, Vitamines, niacin and other secondary metabolites.

Tomato paste for carotenoid extraction may be produced by a method as described, for example, in WO 2003/90554.

The extraction of the carotenoids including, for example, lycopene, lutein, alpha-caroten, beta-carotene, astaxanthine or zeaxanthin or precursors can be achieved by methods generally known in the art. Taungbodhitham et al., Food Chemistry, 63(4): 577-584, 1998 has evaluated suitable extraction method for a wide range of sample matrices in carotenoid analysis, inter alia, using canned tomato juice as a representative sample. Furthermore, an improved lycopene extraction from tomato peels using cell-wall degrading enzymes is described by Lavecchia and Zuorro (European Food Research and Technology, 228:153-158, 2008). Another method is described in U.S. Pat. No. 5,897,866 teaching a process for the extraction of lycopene using phospholipid in the extraction medium.

EP 1103579 discloses a method for lycopene extraction from tomato, grapefruit, watermelon, guava and papaya, which aims at improving the yield of extraction of lycopene. This method essentially comprises the steps of removing the impurities and water from the product by subjecting the product to at least one washing with boiling ethanol, said ethanol having a water content from 20 to 30%, extracting the purified product by subjecting said product to at least one extraction with boiling ethanol having an alcohol content of at least 92%, recovering the ethanol solution and cooling said solution to a temperature around the room temperature to obtain lycopene crystals and filtrating said solution to recover the lycopene crystals.

For products obtained from a tomato plant according to the present invention the first washing step, which essentially serves to remove pesticidal residues, may be avoided due to the reduced amount of pesticides to be used for controlling Orobanchaceae parasites in *Orobanche* resistant tomato plants according to the invention.

The content of the carotenoids in the tomato fruits grown on *Orobanche* resistant tomato plants according to the present invention, may be determined by methods known by a person skilled in the art. An example for such method is described by Fish et al, Journal of Food Composition and Analysis, 15 (3): 309-317, 2002 providing a quantitative assay for the amount of lycopene using reduced volumes of organic solvents. Moreover, Bicanic et al., Journal of the Science of Food and Agriculture, 85 (7): 1149-1153, 2005 presented a method which allows the quantification of lycopene in tomato products by comparing the performances of a proposed direct photothermal method and high-performance liquid chromatography.

EXAMPLES

A. Materials
A.1 Plants
   All experiments were carried out with
   Tomato line M-82, which was obtained from "Tarsis" Agricultural Chemicals Ltd.
   Tomato line M-82 was selfed several times and F4 and F5 plants were used for all experiments.

Tomato line ORT-10, resistant to Orobanchaceae, which was obtained from strain M-82 by mutagenesis using the Fast Neutron method.

Tomato line ORT-10 is deposited with NCIMB under accession number NCIMB 41586.

A.2 Orobanchaceae Strains

All experiments were carried out with the following strains:

O. aegyptiaca seeds were collected from parasitized tomato plants from a field located near Kibbutz Bet Hashita and Eden experimental station located in the Beit Shean valley.

O. cumana seeds were obtained from O. cumana inflorescences parasitizing sunflower at the Jezreel vally.

O. cernuaseeds were obtained from O. cernua_inflorescences parasitizing tomatoes at Bet Dagan.

O. ramosa seeds were obtained from O. Ramosa inflorescences parasitizing potatoes at the Golan Heights.

The Orobanche spp. seeds were separated and dried in glasshouse for a month and then sieved through mesh (30 micron mesh size).

The seeds were stored in the dark at 4 C.° until use.

A.3 Plant Cultivation

Soil Mixture

The soil mixture used for cultivation of tomato plants consisted of sand, red clay and vermiculite No. 2 (Agrical, Habonim), in a volumetric ratio of 1:1:1 (v:v), with the addition of fertilizer (Osmocote) 0.6%.

Soil preparation for this work consisted of 2 or 4-liter plastic pots (Tefen Nachsholim).

Cultivation Conditions

Orobanche seeds were added to each liter of the soil mixture in a concentration appropriate for the intended experiment. The above mentioned ingredients were mixed by rotating them in a cement mixer for 10 minutes until a homogenous mixture was obtained. Control pots did not contain Orobanche seeds. The experimental plant pots were placed in a net house and drip irrigated. Fertilizer, water and pesticides were administered as needed.

B. General Methodology

B.1 Description and Phenotyping of Parasites

The extent of parasite infestation and effect of temperature on Orobanche mediated damage was determined by co-cultivating tomatoes and Orobanche strains in pots and polythene bags, respectively.

B.1.1 Trials in Polythene Bags

For determination of Orobanche resistance of the tomato lines tested and of the parasite range, experiments were carried out in polythene bags. Two strains of tomato plants (the sensitive strain M-82 and the resistant line ORT-10) were used in these polythene bag trials.

Disinfection of Polyethylene Bags.

Orobanche seeds were placed in empty seed sachets and soaked in 70% ethanol for 90 seconds. Immediately afterwards they were soaked in sodium hypochloride 1% with the addition of TWEEN 20 at a concentration of 0.01% for 12 minutes. The bags were rinsed three times in distilled water and twice in sterile water. For each experimental trial, the bags and Petri dishes were treated as stated above.

Growing System in Polyethylene Bags PEB

The nylon bag growing system enabled observation of the host roots and determination of the initial stages of Orobanche infestation, from seed germination, attachment to the host roots, penetration of the host roots, to flowering of the parasite.

The method was carried out as described in Hershenhorn et al. 1996,

Tomato seeds of sensitive strain M-82 and resistant line ORT-10 were germinated on seedling trays containing soil and vermiculite (1:1) to obtain plant seedlings.

After 4 days of growth on the seedling trays tomato shoots emerged from the seeds; the roots were rinsed with distilled water twice, and transferred to plastic polyethylene bags containing glass microfiber filters GF/A (Whatman) and nutrient solution on the bottom. Sterilized Orobanche seeds were evenly distributed on the glass microfiber filters. One tomato seedling was inserted into each bag, and the root system was dispersed on the glass microfiber filters among the Orobanche seeds. The bags were then placed in a dark box such that the foliage of the plants was exposed to the light and the roots remained in darkness.

The boxes were held under long-day conditions of 16 hours light and 8 hours darkness at a temperature of 25° C. The plants were supplied with nutrients by injection of a nutrient solution as needed into each bag according to Hoagland and Arnon (1950).

Contents of Hoagland matrix media:

$Ca(NO_3)_2.4H_2O$ –3 mM
$KCl$ –5mM
$MgSO_4.7H_2O$ –2.2 mM
$KH_2PO_4$ –2 mM
$H_3BO_3$ –46.3 μM
$MnCl_2.H_2O$ –9.1 μM
$ZnSO_4.7H_2O$ –0.8 μM
$CuSO_4$ –0.3 μM
$Na_2MoO_4.2H_2O$ –0.1 μM

B.1.2 Trials in Growing Pots

All experiments carried out in pots were conducted with five replicates, unless otherwise indicated.

Tomato seeds of two lines, M-82 and ORT-10, were germinated on growing trays and after one month, transferred to pots. The experimental observations included:

1. Direct inspection of the interaction of M-82 and ORT-10 with the Orobanche parasite in the soil.
2. Determination of the resistance of the 2 tomato lines to different levels of seed concentration of O. aegyptiaca in the soil.
3. Determination of the range of parasitic activity of O. aegyptiaca on M-82 and ORT-10.
4. Determination of the effect of temperature on levels of O. aegyptiaca parasitism levels on the sensitive and resistant lines.
5. Determination of the effect of different plant structures present in the two tomato lines on the parasitism of different strains of Orobanche.
6. Determination of the inheritance patterns of resistance traits.

Example 1

Determination of Resistance Phenotype 1.1 Parameters Indicative of Tomato Development The purpose of this experiment was to investigate, how the roots of tomato line ORT-10 interact with the Orobanche parasite in comparison to line M-82 and what the consequences are for the development of the tomato lines and the parasite, respectively.

In order to directly observe the resistance of ORT-10 and the response of the plants and it's roots to O. aegyptiaca in comparison with plants grown in pots uninfected with Orobanche seeds, the resistant line ORT-10 and the sensitive line M-82 were planted in infected and uninfected soil, respectively.

The germination of *Orobanche* seeds, attachment of the parasite to the root, the further development of the tomato lines and the *Orobanche* plants until flowering was recorded. The effect of the presence of *Orobanche* seeds in the soil on the development of the two tomato lines was determined through measurement of the following parameters:

foliage height of the tomato plants
wet weight of the foliage
wet weight of the roots
dry weight of the roots The experiment was carried out in greenhouses during a normal day of 14 hours light for a period of 90 days. Seedlings of the two tomato lines were grown in 2 liter pots with soil infected with *O. aegyptiaca* at a concentration of 20 ppm. The experiment included the following treatments which were carried out with 30 replicates per (pots) treatment.

A. ORT-10 in *O. aegyptiaca* infected soil.
B. ORT-10 in uninfected soil.
C. M-82 in *O. aegyptiaca* infected soil.
D. M-82 in uninfected soil.

At intervals of one week, beginning at week 3 after planting and ending in week 8, 5 pots were taken from each treatment, and the height and wet weight of the tomato plants were determined. After cutting of the plant at the root neck, the root system of the plants was rinsed with water to remove the soil, and the number of *Orobanche* plants colonizing the roots was counted.

Wet weight of the roots and the *Orobanche* plants was measured by drying the plant material in an oven at 70° C. for 70 hours and determining the dry weights.

Tomato Plants a. Foliage Height.

Until week 4 after planting the foliage height is similar for both tomato lines independent of whether they are grown in soil infected or uninfected with *Orobanche* seeds. Development of M-82 plants in non-infested soil in terms of foliage height is better than in infected soil and is better than the development of ORT-10. There is no difference found in the development of ORT-10 in infected or uninfected soil.

b. Wet Weight of Foliage.

Similar observations were made for the wet weight parameter. No difference in wet weight of ORT-10 could be observed for plants growing on infected or uninfected soil.

Up to week 6 there is also no difference in foliage weight of M-82 grown on infected and uninfected soil, respectively. After week 6, wet weight of foliage of plants grown on infected soil was lower than the foliage weight of plants grown on uninfected soil. (66-208 grams per plant, at week 8 after planting). Similar results were noted when dry weights were compared (results not shown).

c. Wet Weight of Roots.

Up to week 7 after planting, no significant difference was noted between plants growing in soil infected or uninfected with *Orobanche*. For the resistant line, this was still the case at the end of the trial.

In contrast thereto, the weight of roots of sensitive M-82 plants grown in infected soil was lower than for plants grown in uninfected soil.

d. Dry Weight of Roots.

At the end of the experiment, a dry weight of 9 grams was determined for the roots of the resistant plant line grown in uninfected soil, which was the highest dry weight recorded. The corresponding dry weight of resistant plants grown on infected soil was very similar (7 grams).

The same dry weight of about 7 gram could be determined for the sensitive tomato line grown in uninfected soil.

For the sensitive line grown on infected soil however, already at week 6 a dramatic loss in dry weight could be observed. The dry weight recorded was 2 grams, which is 4.5 times less than that of roots of resistant plants, when grown in infected soil.

1.2 Parameters Indicative of *Orobanche* Development

*Orobanche* Plants a. During the first 4 weeks after planting, the weights of *Orobanche* plants grown on the sensitive and the resistant line were similar. Starting from week 5 to the end of the experiment, there was a drastic increase in wet weight of *Orobanche* plants grown on the sensitive tomato line, which was 7.5 times greater than that found for *Orobanche* plants grown on the resistant line.

b. Similar results were obtained when dry weights were determined. After a moderate increase in dry weight of *Orobanche* plants grown on the sensitive tomato line compared to plants grown on the resistant line, a 3 times higher value could be determined for the *Orobanche* plants grown on the sensitive line at the conclusion of the experiment.

Tomato Roots Infected with *Orobanche* a. During the first 5 weeks after planting, almost no differences were noted between wet weight of tomato roots+wet weight of *Orobanche* in the 2 tomato lines when grown on infected soil compared with uninfected soil.

From week 5 and until the end of the experiment a significant increase in wet weight of tomato roots+wet weight of *Orobanche* was noted.

In the sensitive tomato line, when grown on infected soil, the weight reached 110 grams per plant.

In the resistant plant, when grown on infected soil, the wet weight reached 70 grams.

The wet weight of the roots of both strains was similar for plants grown on uninfected soil, and reached 60 grams.

Example 2

Effect of Concentrations of *O. aegyptiaca* on the Resistance

In the growing experiments with plants of line ORT-10, no emergence of inflorescences of the *Orobanche* parasite could be observed when grown in soil infected with 20 ppm *Orobanche* seeds. Tomato plants of line ORT-10 exhibited full resistance to the *Orobanche* parasite at this concentration.

Even at increasing concentrations (50-100 ppm), the level of parasitism in the resistant strain remains low and similar to that of the commercial strain at 20 ppm.

Resistance of tomato to Orobanchaceae can be influenced by different factors. In this experiment, full resistance of ORT 10 was not preserved at all Orobanchaceae concentrations, and from concentrations of 50 ppm and over there was a slight decrease of resistance of tomato plants to Orobanchaceae.

For ORT-10, *Orobanche* inflorescences were barely observed. At soil containing 20 ppm *Orobanche* seeds no parasites were recorded on the roots and a low level of parasites were counted at broomrape seed levels of 50 and 100 ppm. By the end of the experiment the no. of *Orobanche* flowers per plant was 0.5-0.8 respectively.

For M-82, at 20 ppm broomrape seeds per Kg soil, 0.8 flowers were seen by the end of the experiment. At *Orobanche* seed levels of 50 and 100 ppm 2.2 and 2.6 flowers per plant were recorded, respectively.

Example 3

Pathogenicity of Different *Orobanche* Species

The purpose of the experiment was to measure the resistance levels of M-82 and ORT-10 to different species of Orobanche commonly found in cultivated fields in Israel (*O. ramosa, O. cumana, O. crenata, O. cernua, O. aegyptiaca*): In particular, it was an objective to determine whether *Orobanche* species other than *O. aegyptiaca*, are able to parasitize ORT-10, and to compare the responses with that observed in the sensitive tomato line M-82.

In order to ascertain the effect of the *Orobanche* pathogen on the plant, uninfected plants of both strains were included as controls.

The experiment was carried out under net house conditions under normal day of 14 hours light for a period of 90 days. Seedlings of the two lines of tomato were grown in soil infected with *Orobanche* at a concentration of 10 ppm. At the conclusion of the experiment the soil was washed out from each plant and the root system of each plant was checked for infection with *Orobanche* species.

The following parameters were determined for plants infected with the different Orobanchaceae strains:
  root weight,
  "spider" formation,
  no. of flowers
  weight of *Orobanche* on sensitive and resistant plants Statistical analysis was carried out by the ANOVA test. The lines indicate standard deviations. 5 replicates for each treatment of resistant strain ORT-10 and sensitive strain M-82 were used in the experiment.

No. of Broomrape Flowers Per Plant

The no. of flowers per plant for the sensitive tomato line was similar for plants grown on soil infected with the following pathogens: *O. aegyptiaca, O. crenata, O. cemua* with about 7-10 flowers per plant.

When the same plants were grown on soil infected with *O. ramosa* the number of flowers was lower and reached approx. 3 per plant.

No flowers appeared on resistant tomato plants grown in soils infected with *O. cumana, O. ramosa* and *O. crenata*, and in soil infected with *O. cemua* and *O. aegyptiaca*, only 1 flower appeared per plant.

Weight of Orobanchaceae Per Plant

The weight of *Orobanche* plants on the roots of the 2 tomato lines grown in soil infected with *O. aegyptiaca* and *O. cemua* were similar.

At no stage of growth did *O. crenata* or *O. ramosa* appear on the roots of the resistant plant.

Example 4

Effect of ORT-10 and M-82 Extracts on Germination of *O. aegyptiaca*

4.1 Preparation of Extracts

The purpose of the experiment was to estimate the phytotoxic activity of extracts prepared from resistant and sensitive strains, by estimating the level of *O. aegyptiaca* seed germination delay in Petri dishes, and determining seed germination of *O. aegyptiaca* after treatment with a solution of G24. The experiment was carried out in a greenhouse under long day conditions, 14 hours daylight, for a duration of 90 days. Both lines of tomato were grown in 4 liter pots in soil infected with *O. aegyptiaca* at a concentration of 10 ppm. As controls, both lines of tomato were grown in 4 liter pots in uninfected soil. In this experiment, large 4 liter pots were used in order to obtain large root volumes to provide large amounts of extract. The experiment was conducted with 10 replications per treatment. The treatments were the following:
  A. ORT-10 in *O. aegyptiaca* infected soil.
  B. ORT-10 in uninfected soil.
  C. M-82 in *O. aegyptiaca* infected soil.
  D. M-82 in uninfected soil.

Two months after the commencement of the experiment, the soil was gently washed from the pots, root systems were weighed, and then stored at 20° C. until extraction.

4.2 Differential Extraction

In a first extraction step, organic extracts were made from the tomato roots in hexane.

Root cuttings (10 g) are homogenized in 60 ml of hexane. The homogenized roots in hexane were then gently stirred for one hour at room temperature and subsequently filtered via Whatman no. 2 filter paper under vacuum into a Buchner flask.

The homogenate remaining on the filter paper after filtration is re-extracted with chloroform by the same method for one hour. Similar extractions are then carried out in ethyl acetate, methanol, and, water, respectively.

The different extracts were then dried under reduced pressure at a temperature of 30° C., in an evaporator (Buchi, Switzerland), and after drying, the dry weight was determined of each extract.

4.3 Biological Assay

The purpose of the biological assay was to determine the activity of each of the different extracts in preventing *Orobanche* seed germination.

*Orobanche* seed germination was carried out according to the method of Hershenhorn et al (1997), under sterile conditions, in Petri dishes at a diameter of 5 cm, lined with Whatman paper (diam 4.5 cm) soaked in 1 ml. water. Discs, 0.5 cm dia. were placed on the filter paper and on each such disc sterilized *Orobanche* seeds were placed.

After 7 days of preconditioning for germination, under humid conditions, and a temperature of 25° C., the discs with the *Orobanche* seeds were transferred to new Petri dish containing filter papers saturated with water to maintain humidity. To this new plate 200 μl of GR 24 was added, at a concentration of 3 ppm. After 7 days from the addition of G24, seeds of *Orobanche* began to germinate.

Six Petri dishes of 5 cm diameter were prepared, and on each plate 2 discs with *Orobanche* seeds were placed. To each of the plates 10 μl of the extract dissolved in 2% ethanol solution was added. Ethanol solution (2%) was used as a control.

After addition of the extracts prepared according to 4.1 above, the plates were incubated at 25° C. for 48 hours. After 48 hours the effect of different extracts on seed germination levels of *Orobanche* was estimated. The observations were carried out by means of a binocular microscope.

Example 5

Paper Envelopes for *Orobanche* Seed Germination as a Reaction to Stimulants

The purpose of the experiment was to determine if the mechanism of resistance of ORT-10 to *Orobanche* spp. is due to a blockage of stimulant synthesis in the plant or of stimulator secretion in comparison with *Orobanche* sensitive strain M-82, or due to release of a substance which retards stimulant activity, or due to secretion of toxic substances which effect germination of the *Orobanche* pathogen. Either or both of these two processes could be reasons why *Orobanche* does not parasitize the roots of ORT-10.

The determination between these three possibilities was carried out in the following three experiments. Each possibility was investigated by a separate experiment. In all cases, paper envelopes (soaked or unsoaked in G24 solution) containing *Orobanche* seeds were embedded among ORT-10 and M-82 roots such that the plant roots grew alongside or into the envelopes.

5.1 The Ability of ORT-10 and M-82 to Germinate *O. aegyptiaca*.

Unconditioned sterilized seeds of *O. aegyptiaca* were distributed on GFA paper of 5×5 cm. (70 seeds per square centimeter). The paper was folded into 2 and stapled closed. The paper envelope was embedded in 2 liter pots filled to ⅓ rd with uninfected soil. A tomato plant was planted between two envelopes with a gap between tomato roots and the envelopes. Uninfected soil was then added to the pot until full. The experiment was carried out under conditions of natural light for 21 days, with light for approximately 14 hours per day. The experiment included ORT-10 and M-82 and control pots with envelopes but without plants as a control for spontaneous *Orobanche* seed germination. Two weeks after planting, the envelopes were withdrawn from the pots, and one envelope from each pot was randomly examined through a binocular microscope to ascertain the start of germination.

Each week, for a period of 3 weeks beginning two weeks after planting, the soil was rinsed from five experimental pots and one control pot. The GFA paper envelopes with the *Orobanche* seeds were removed opened and the percentage of seed germination was recorded with the aid of a binocular microscope.

In the control pots with embedded envelopes containing *Orobanche* seeds but no tomato plants, there was no spontaneous germination of *Orobanche* seeds.

The percentage of *Orobanche* seed germination in envelopes pretreated with G24 and embedded in soil close to M-82 plants was high, between 76% to 85%. In comparison, the percentage of non G24 pretreated *Orobanche* germination found in envelopes embedded with ORT-10 plants was insignificant (0.7%) The germination levels found in the G24 pretreated envelopes and embedded with ORT-10 plants reached 85%.

TABLE 1 percentage of *Orobanche* seed germination

| 14DAP | % germination |
|---|---|
| M-82 (−GR) | 79.9 ± 6.6 |
| M-82 (+GR) | 75.5 ± 0 |
| ORT-10 (−GR) | 0.7 ± 0.114 |
| ORT-10 (+GR) | 85.1 ± 5.565 |
| Control | 0 |

5.2 The Ability of ORT-10 and M-82 to Release Active Stimulatory Substances.

Paper envelopes were prepared with seeds that had undergone preconditioning as described. To the first half of the envelopes containing the *Orobanche* seeds 500 μl of the synthetic stimulant G24 was added at a concentration of 3 ppm; to the second half of the envelopes 500 μl of sterile water was added. The envelopes were placed in growing pots together with ORT-10 or M-82 as described above. The experiment was carried out under conditions of natural light for 14 days, with light for approximately 14 hours per day.

Two weeks after planting the paper envelopes containing the *Orobanche* seeds were removed from the pots and the percentage of *Orobanche* seed germinated was determined using a binocular microscope. The observations were carried out from the centre of the paper along the root length, and the number of seeds were counted and correlated with the number of germinated seeds.

5.3 The Ability of ORT-10 and M-82 to Secrete Toxic Substances Which Damage Germinating Ability of Orobanchaceae.

Paper envelopes were prepared with seeds that had undergone preconditioning as described. To the first half of the envelopes containing the *Orobanche* seeds 500 μl of the synthetic stimulant G24 was added at a concentration of 3 ppm; to the second half of the envelopes 500 μl of sterile water was added. The envelopes were placed in growing pots together with ORT-10 or M-82 as described above.

On day 5 and day 10 from the start of the experiment, 100 ml of the synthetic stimulant GR24 at a concentration of 2 ppm was added to each pot containing plants which had sprouted from ORT-10 or M-82 containing envelopes which had been presoaked in GR-24. The experiment was carried out under conditions of natural light for 21 days, with light for approximately 14 hours per day. 21 days after planting the paper envelopes containing *Orobanche* seeds were removed from the pots and the percentage of germinated *Orobanche* seeds was determined, using a binocular microscope. The observations were carried out from the centre of the paper along the root length, and the number of seeds were counted and correlated with the number of germinated seeds.

Example 6

Germination Bioassay for *Orobanche* Seeds 6.1 Exudate Collection and Analysis:

Two tomato cultivars, M82 and mutant ORT-10, were grown in a mixture of sand and perlite (1:1, v:v) under greenhouse conditions (25/20° C. day/night). After 4 weeks of growth the soil from the pots were removed gently under tap water and the root system, still connected to the foliage, was immersed in 10 ml of double distilled water (DDW) in a test tube covered with aluminum foil (to exclude light). After 24 hrs, the water in the test tubes was collected and the volume of the root exudates and root fresh weight for each plant were determined. The exudates were standardized to equal conc. (ml of exudates per gram of root weight). *Orobanche* seeds were preconditioned on glass fiber filter paper discs (9 mm) which were kept on a moist Whatman filter paper for 6 days in the incubator at 28° C. before used. At the seventh day, the seeds on the discs were transferred to a fresh Petri plate lined with moist filter paper rings on its wall and allowed to dry for 20 minutes in a sterile hood cabinet. Forty micro liters of root exudates was added to each disc. The discs were then kept in the incubator for 6 days and the percentage of seed germination was calculated at the seventh day. Synthetic germination stimulant GR 24 (5 ppm) was used as a positive control and water as a negative control.

TABLE 2

Seed Germination Rate in a Germination Bioassay for *Orobanche* Seeds

| Tomato Line | Seed Germination Rate (%) |
|---|---|
| M82 | 60.8 + 1.25 |
| ORT 10 | 0 |

6.2 Root Extract Preparation and Analysis:

The roots of the two tomato lines e.g. M82 and ORT10 were grown for four weeks, and were carefully removed and washed as described above (Exudate collection). The roots were gently dried using paper napkins and 0.1 g of root was cut and stored in liquid nitrogen. These roots were ground in pestle and mortar using liquid nitrogen and then extracted with 2 ml of ethyl acetate. The solution was transferred into eppendof tubes, vortexed and sonicated in an ultra sonic bath for 10 minutes. The slurry was then centrifuged at 1,350 g for 10 minutes. The supernatant was removed and equal amount of DDW was added to the precipitate. The supernatant was evaporated using a speed vac centrifuge for 10 minutes. The solution was then used for the bioassay tests, as described in the above protocol.

TABLE 3

Analysis of Root Extract on Seed Germination Rate in a Germination Bioassay for *Orobanche* Seeds
Root Extract Analysis

| Tomato Line | Seed Germination Rate (%) |
|---|---|
| M82 | 72.4 + 1.7 |
| ORT 10 | 0 |

Example 7

Grafting Experiments

The sensitivity of all possible combinations of grafting of M82 plants and resistant ORT 10 plants to *O. aegyptiaca* were tested.

In particular, the following four (4) types of grafts were tested:
sensitive on sensitive M-82/M-82,
resistant on resistant ORT-10/ORT-10,
resistant on sensitive ORT-10/M-8; 2 and
sensitive on resistant M-82/ORT-10.

As a control, sensitive (M82) and resistant plants (ORT-10) which had not undergone grafting were used. The trial was carried out under netting and long day conditions with 14 hours daylight, for duration of 60 days.

Figure 1:
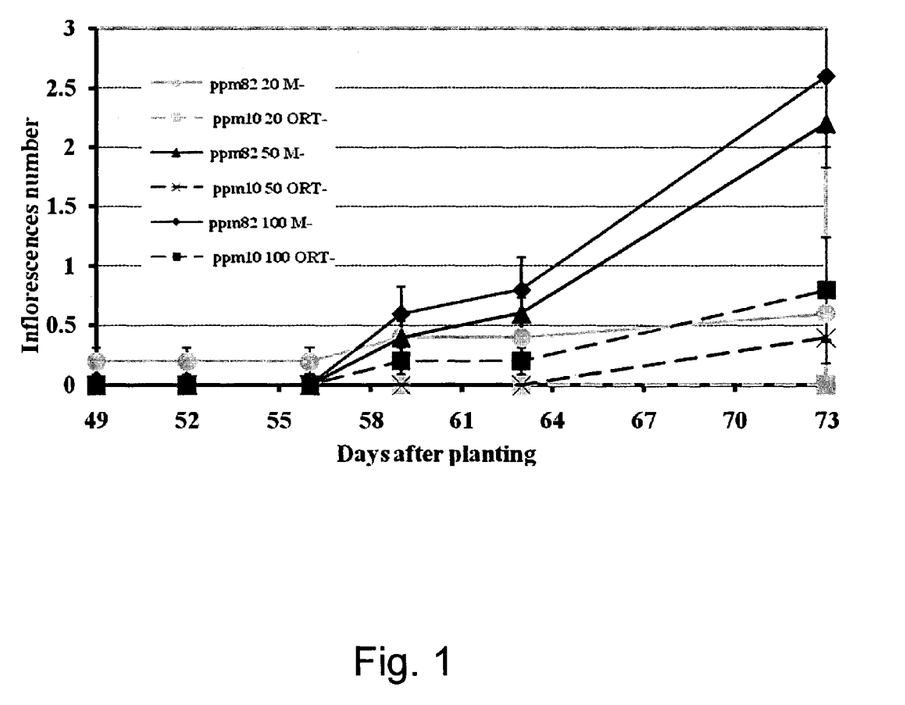
FIG. 1 shows the effect of *O. aegyptiaca* seed concentration in the soil on number of *Orobanche* inflorescences in tomato lines ORT-10 and M-82. Statistical analysis was according to the ANOVA test. The vertical lines represent standard deviations. The experiment included 5 replicates of each treatment.
Figure 2:
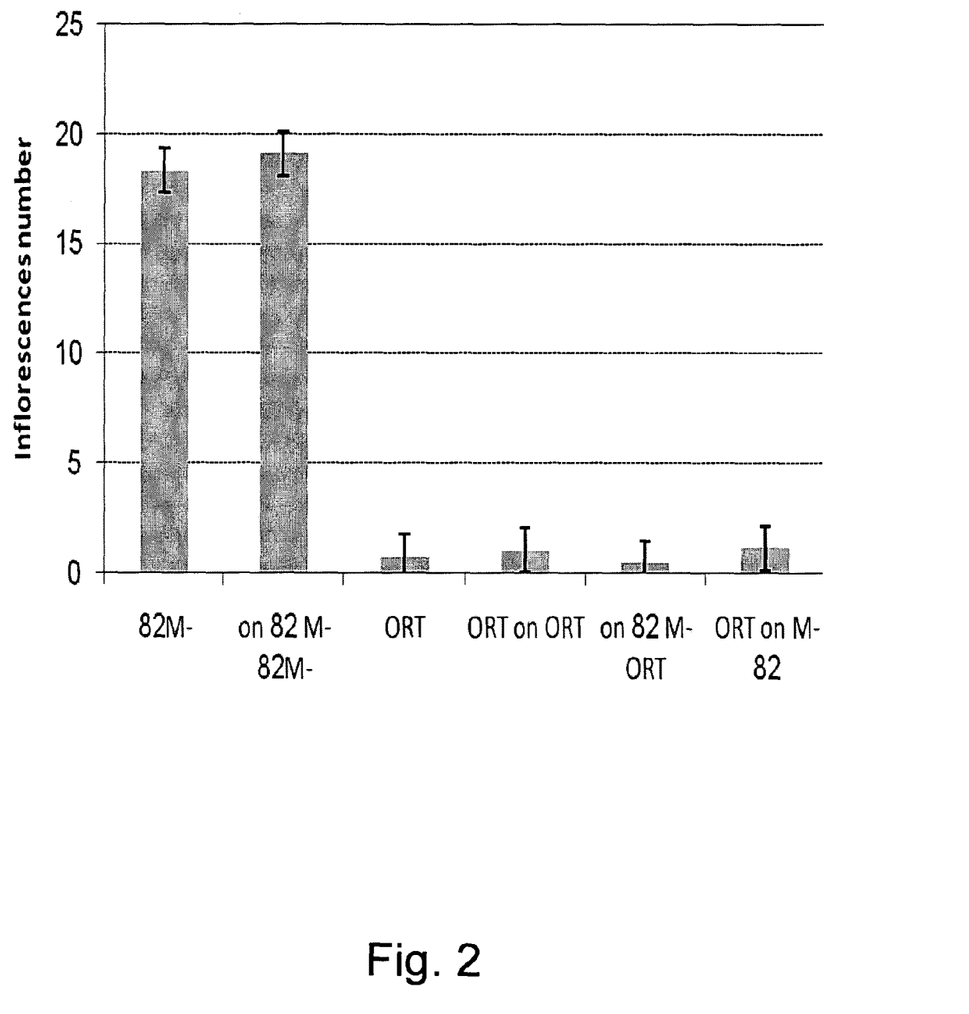
FIG. 2 shows the effect of grafting on the number of *O. aegyptiaca* inflorescences on the host plant. Statistical analysis was conducted according to the ANOVA test. The vertical lines represent standard deviations. The experiment included 15 replicates of each treatment.

The experiment was carried out in 2 liter pots containing soil infected with *O. aegyptiaca* seeds at a concentration of 10 ppm. The number of the parasite inflorescences that emerged above soil was counted at the conclusion of the experiment:

The results of the grafting experiment are summarized in FIG. 2.

The number *Orobanche aegyptiaca* inflorescences per counted on M82 and on self grafted M82 was 17-18 parasites per plant. All combinations of grafted plants with ORT 10 were resistant to *Orobanche* with no more than 2 *Orobanche aegyptiaca* inflorescences per host plant.

Example 8

Genetics of *Orobanche* Resistant Inheritance in Tomato 8.1 Characterization of Orobanchaceae Resistance.

The purpose of the experiment was to ascertain the number of genes controlling the resistance phenotype in *Orobanche* resistant tomato lines, and characterizing these genes (i.e. whether recessive or dominant). The experiment was carried out under net house conditions in natural daylight averaging 14 hours per day for the duration of 90 days. The resistance inheritance of to *O. aegyptiaca* was studied based on 3 tomato lines which were derived from the following crosses:
A. Fertilization between ORT-10 and M-82 to obtain F1 (ORT-10').
B. Self-fertilization of F1 (ORT-10') to obtain F2.
C. Plants derived from F2 which had undergone backcrossing with ORT-10.

In the experiments plants from sensitive and resistant lines were used, and 3 populations of plants were used which were derived from crossing F2 of resistant tomato plants to parentals from the resistant line.

Statistical analysis was carried out using the ANOVA test. The lines represent standard deviations. In this experiment, 84 replicates were used for M-82, 84 replicates were used for ORT-10 F5, 77 replicates fro ORT-10 2F2BC1, 82 replicates for ORT-10 4F2BC1, 106 replicates for ORT-10 6F2BC1.

The experiments were run in parallel with ORT-10 and M-82.

Experiments were carried out in 2 liter pots containing soil infected with *O. aegyptiaca* at a concentration of 10 ppm. The *Orobanche* parasite was counted twice a week for each pot, beginning from the first day after emergence of *Orobanche* shoots. At the conclusion of the experiment the soil was washed off from the plants and the root system of each plant was examined to determine the extent of parasite infestation by *Orobanche*.

8.2. Inheritance of Resistance to *Orobanche* in the Resistant Tomato Strain.

Examination of ORT-10 and M-82 plants reveals that line ORT-10 is distinguished from line M-82 by the presence of resistance to *O. aegyptiaca* and other *Orobanche* species. This difference between the 2 tomato lines is manifested in the following parameters:

Height and weight of foliage, weight of roots, weight of *Orobanche* parasite and no. of colonizing *Orobanche* parasites.

One method for examining a gene which confers resistance to *Orobanche* is to quantify the no. of plants affected by the pathogen. On day 41 after planting, *Orobanche* inflorescences began to appear above ground. The rate of *Orobanche* inflorescences appearance during the first week was very fast and by the end of the experiment 91% of the plants were infected.

In the resistant strain, the rate of *Orobanche* inflorescences appearance was low up to day 51, and from then until the end of the experiment the percentage of affected plants was less than 50%. In both populations of plants that were back crossed, 4F2BC1 and 2F2BC1, a rise in the number of affected plants beginning from day 41 until the end of the experiment reached 70% In population 4F2BC1 the rate of Orobanchaceae flowers appearance was moderate and reached 28%, this rate of appearance of Orobanchaceae flowers is similar to that obtained with ORT-10.

Apart from testing for the percentage of plants infected with the *Orobanche* pathogen, the no. of pathogens per host plant was estimated for all strains. From day 41 until the end of the experiment a steep rise was noted in the no. of *Orobanche* plants per sensitive tomato plants reaching 6.

Also for two of the back-cross populations, 6F2BC1 and 2F2BC1, a moderate rise to 2 *Orobanche* plants per tomato plant could be observed. In the third population, 4F2BC1, the no. of *Orobanche* plants did not exceed 1 per tomato pant. The same effect is seen with the resistant strain ORT-10.

8.3 Inheritance of Resistance to *Orobanche* in Resistant Tomato Line ORT-10.

In order to determine whether the resistance phenotype is transmitted by a single gene or multiple genes, and whether inheritance is dominant or recessive the results of the previously reported experiments were carefully analyzed. As a result of this analysis we were able to ascertain the type of inheritance and the number of genes involved in resistance. The dynamics of the number of plants from the infected population and the percentage of the plants damaged is very consistent in ORT-10 resistant plants. The percentage of damaged plants from the infected population was 75%, that is to say, 25% were not damaged. This result indicates Mendelian inheritance of one recessive gene.

Example 9

Resistance of Screen-Breed Progenies

The potential to cruse-breed the resistance trait to other tomato backgrounds was evaluated by crossing the F5 generation of tomato line ORT10 with *Solanum pimpinellifolium* (LA-1589). The F1 plants were selfed to produce F2 progeny. Plant number 3 from F2-27 constituted the population which was later used for our screening experiments. F3 of single plant families from these F2 were tested under field conditions to validate the stability of resistance in the next generation and to identify F3 families that are resistant to the parasite (*O. aegyptiaca*) under field conditions.

The experiment was carried out in kibbutz Mevo-Hama on the sought part of the Golan Heights, Israel. Two replicates of 190 F3 families were planted, 10 individual plants in each family in each replica. Plants were planted 1.2 m apart (in the raw) with one raw on each raised bed (1.8 m wide). After 35 days from planting, *Orobanche* inflorescences became visible above ground in susceptible plants. 23 families were found to tolerate *Orobanche* in both replicates, 20 families showed resistance in one replicate but not the other, 8 families became infected very late relative to the controls, 24 families showed resistance in 50%. The rest of the families showed a susceptible phenotype.

TABLE 4

| Category | # plants | |
|---|---|---|
| All 10 plants are resistant in both replicates (20 plants) | 23 | 12% |
| All 10 plants are resistant in one replica but, not in the other rep | 20 | 10.5% |
| Was infected late in both replicate | 8 | 4.2% |
| Half of the plants resistant in each family | 24 | 13% |
| Very susceptible plants | 11 | 6% |

Deposit

The following seed sample of *Solanum lycopersicum* line ORT-10 was deposited with NCIMB, Ferguson Building, Craibstone Estate, Bucksburn, Aberdeen AB21 9YA, Scotland, UK on 22 Oct. 2008 under the provisions of the Budapest Treaty in the name of Zeraim Gedera Ltd, PO Box 103, 70750 Gedera, Israel and in the name of the State of Israel, Ministry of Agriculture & Rural Development, Agricultural Research Organization (A.R.O.), Volcani Center, P.O. Box 6, 50250 Bet Dagan, Israel:

| *Solanum lycopersicum* seed line designation | Deposition date | Accession No |
|---|---|---|
| ORT-10 | 22$^{nd}$ Oct. 2008 | NCIMB 41586 |

REFERENCES

Akhtouch, B., J. Muñoz-Ruz, J. M. Melero-Vara, J. M. Fernández-Martínez, and Domínguez, J. (2002). Inheritance of resistance to race F of broomrape in sunflower lines of different origins. Plant Breed. 121: 266-268.

Alonso L. C. (1998). Resistance to *Orobanche* and resistance breeding: a review. In: Wegmann K, Musselman L J, Joel D M, eds. *Current problems of Orobanche research. Proceedings of the 4th International Workshop on Orobanche Research*, Albena, Bulgaria, 233-257.

Bicanic et al., Journal of the Science of Food and Agriculture, 85 (7): 1149-1153, 2005

Dörr, I and Kollmann, R. (1974). Structural features of parasitism of *Orobanche*. I. Growth of the haustorial cells within the host tissue. Protoplasma 80:245-259.

Eizenberg, H., Plakhine, D., Hershenhorn, J., Kleifeld, Y. and Rubin, R. (2003). Resistance to broomrape (*Orobanche* spp.) in sunflower (*Helianthus annuus* L.) is temperature-dependent. Journal of Experimental Botany 54: 1305-1311.

Eizenberg, H., Plakhine, D., Hershenhorn, J., Kleifeld, Y., and Rubin, B. (2004). Variation in response of sunflower cultivars to the parasitic weed broomrape. Plant Disease 88: 479-484.

Fish et al, Journal of Food Composition and Analysis, 15 (3): 309-317, 2002

Goldwasser, Y., Hershenhorn, J., Plakhine, D., Kleifeld, Y. and Rubin, B. (1999). Mechanisms involved in the resistance of purple vetch (*Vicia atropurpurea*) to Egyptian broomrape (*Orobanche aegyptiaca*). Physiological Molecular Plant Pathology 54: 87-96.

Hoagland, D. R. and Arnon, D. I. (1950). The water-culture method for growing plants without soil. California Agriculture Experiments Station. Circular 347:32.

Hershenhorn, J., Goldwasser, Y., Dina Plakhine, Herzlinger, G., Golan, S., Russo, R. and Kleifeld, Y. (1996). Role of pepper (*Capsicum annuum*) as a trap and catch crop for control of *Orobanche aegyptiaca* and *O. cernua*. Weed Science 44: 948-951.

Hershenhorn, J., Plakhine, D., Goldwasser, Y., Westwood, J. H., Foy, C. L. and Kleifeld, Y. (1998). Effect of sulfonylurea herbicides on early development of Egyptian broomrape (*Orobanche aegyptiaca*) in tomato (*Lycopersicon esculentum*). Weed Technology 12: 108-114.

Joel, D. M., Hershenhorn, J., Eizenberg, H., Aly, R., Ejeta, G., Rich, P. J., Ransom, J. K., Sauerborn, J. and Rubiales, D. (2007). Biology and management of weedy root parasites. Pages 267-349 In J. Janick, ed, Horticultural Reviews, Vol 33. John Wiley & Sons, Hoboken, N.J.

Jorín, J., Peírez-de-Luque, A. and Serghini, K. (1999). How plants defend themselves against root parasitic angiosperms: molecular studies with *Orobanche* spp. In: Cubero J I, Moreno M T, Rubiales D, Sillero J C, eds. Resistance to *Orobanche*: the state of the art. Sevilla, Spain: Junta de Andalucía, 9-15.

Kilchevsky, Alexander; Dobrodkin, Michail (2000). Use of functional male sterility in seed production of tomato hybrids. Acta Physiologiae Plantarum. 22: 232-234.

Labrousse P., Arnaud, M. C., Serieys, H., Berville', A. and Thalouran, P. (2001). Several mechanisms are involved in resistance of *Helianthus* to *Orobanche cumana* Wallr. Ann. Bot. 88: 859-868. Musselman, A. J, (1994), Biology and management of *Orobanche*. Proceedings of the Third International Workshop on *Orobanche* and related Striga research, 27-35.

Lavecchia and Zuorro, European Food Research and Technology, 228:153-158, 2008

Poehlman, J. M. Sleper, D, A. (1995) Breeding Field Crops, 4th Ed., 172-175; Fehr (1987) Principles of Cultivar Development, Theory and Technique, 1: 360-376.

Press, M. C., and Graves, J. D. (1995). Parasitic plants. Chapman and Hall, London. Rieger, R., Michaelis, A, and Green, M. M. (1968). A Glossary of Genetics and Cytogenetics, 3$^{rd}$ ed. (New York: Springer-Verlag,).

Serghini, K., A. Pérez de Luque, M. Castejón-Muñoz, L. Garcia-Torres, and Jorín. J. (2001). Sunflower (*Helianthus annuus* L.) response to broomrape (*Orobanche cemua* Loefl.) parasitism: induced synthesis and excretion of 7-hydroxylated simple coumarins. J. Expt. Bot. 52:2227-2234.

Taungbodhitham et al., Food Chemistry, 63(4): 577-584, 1998

Wegmann, K., von Elert, E., Harloff, H. J., and M. Stadler, M. (1991). Tolerance and resistance to *Orobanche*. p. 318-321. In: K. Wegmann and L. J. Musselman (eds.), Progress in *Orobanche* research. Proc. Workshop on *Orobanche*, Tübingen, Germany.

Wegmann K., von Elert E., Harloff H.-J., Stadler M. (1989) The International Workshop on *Orobanche* Research, Obermarchtal, FRG, August 19-22, 318-321.

Patent Literature:
WO 2003/90554
U.S. Pat. No. 5,897,866
EP 1103579

EMBODIMENTS OF THE INVENTION

1. A tomato plant exhibiting a resistance to a parasitic plant of the genus *Orobanche*, wherein said resistance is controlled by a genetic determinant.

2. The tomato plant of embodiment 1, wherein said genetic determinant is freely transmissible between different tomato plants or lines.

3. The tomato plant of embodiment 2, wherein said genetic determinant shows a Mendelian inheritance.

4. The tomato plant of embodiment 3, wherein said genetic determinant controlling the *Orobanche* resistance is represented by a single gene which shows a recessive inheritance.

5. The tomato plant of embodiment 4, wherein said genetic determinant controls production and/or secretion of a chemical stimulant that causes germination of seeds of a parasitic plant of the genus *Orobanche*.

6. The tomato plant of embodiment 5, wherein production and/or secretion of said chemical stimulant is inhibited.

7. The tomato plant of any one of embodiments 1 to 6, which provides a root exudate which upon application to seeds of a parasitic plant of the genus *Orobanche* leads to a germination rate in a seed germination assay of not more than 5%.

8. The tomato plant of embodiment 7, wherein the parasitic plant of the genus *Orobanche* used in said seed germination assay is a *O. aegyptiaca* plant.

9. The tomato plant of any one of embodiments 7 or 8, wherein the germination rate in the seed germination assay is not more than 2%.

10. The tomato plant of any one of embodiments 7 to 9, wherein the germination rate in a seed germination assay is not more than 0.5%.

11. The tomato plant of any one of embodiments 7 to 10, wherein the germination rate in a seed germination assay is 0%.

12. The tomato plant of any one of embodiments 1 to 6 which provides a root extract upon extraction of root tissue with ethyl acetate, which upon application to seeds of a parasitic plant of the genus *Orobanche* leads to a germination rate in a seed germination assay of not more than 5%.

13. The tomato plant of embodiment 12, wherein the germination rate in a seed germination assay is not more than 2%.

14. The tomato plant of any one of embodiments 12 or 13, wherein the germination rate in a seed germination assay is not more than 0.5%.

15. The tomato plant of any one of embodiments 12 to 14, wherein the germination rate in a seed germination assay is 0%.

16. The tomato plant according to any of the preceding embodiments, wherein said plant is resistant to at least one parasite selected from the group consisting of *Orobanche aegyptiaca, O. ramosa, O. crenata, O. cemua*.

17. The tomato plant of any of embodiment 1 to 16, wherein said *Orobanche* parasite is *O. aegyptiaca*.

18. The tomato plant according to any of the preceding embodiments, which can be obtained from a donor plant comprising a genetic determinant controlling expression of the *Orobanche* resistance phenotype through introgression of said genetic determinant into a recipient plant, which is susceptible to infestations with the *Orobanche* parasite, particularly to infestations of *O. aegyptiaca*.

19. The tomato plant according to embodiment 18, wherein tomato line ORT-10, deposited with NCIMB under accession number NCIMB 41586 is used as a donor plant for the *Orobanche* resistance trait.

20. The tomato plant according to any of the preceding embodiments, wherein said resistance becomes manifest in the behavior of the plant towards an infestation with an *Orobanche* parasite, in that the resistant plant is only affected by a decrease of between less than 5%, particularly of less than 4%, particularly of less than 3%, particularly of less than 2%, particularly of less than 1%, but especially of 0%., in one or more of the parameters selected from the group consisting of plant height, wet and dry weight of the root system, wet and dry weight of the foliage, dry and wet weight of the infested root including the broomrape parasite.

21. The tomato plant according to the preceding embodiment, wherein the wet weight of the *Orobanche* parasite growing on said resistant plant is about 10 times less than that of a parasite growing on a sensitive plant.

22. The tomato plant according to any of the preceding embodiments which is an inbred, a hybrid and/or a male sterile.

23. The tomato plant according to any of the preceding embodiments, wherein said plant contains a genetic determinant controlling expression of the *Orobanche* resistant phenotype, which genetic determinant is obtainable from tomato line ORT-10, deposited with NCIMB under accession number NCIMB 41586.

24. Tomato plant line ORT-10, seeds of which is deposited with NCIMB under accession number NCIMB 41586.

25. A hybrid tomato plant providing *Orobanche* resistance produced by using tomato plant line ORT-10 as a parent.

26. Method of producing an *Orobanche* resistant tomato plant comprising the steps of introgressing from a donor plant comprising a genetic determinant directing expression of the *Orobanche* resistance phenotype into a recipient plant, which is susceptible to infections with the *Orobanche* parasite, particularly to infestations of *O. aegyptiaca*, by (a) crossing said donor plant with said recipient plant to obtain a progeny plant exhibiting the *Orobanche* resistance, (b) screening for and selecting from the progeny plants a plant exhibiting an *Orobanche* resistant phenotype and, optionally, harvesting the resultant progeny seed.

27. The method of embodiment 26, wherein tomato line ORT-10, deposited with NCIMB under accession number NCIMB 41586 is used as the donor plant for the *Orobanche* resistance trait.

28. A method for securing tomato fruit production to a commercially relevant extent in a geographical area with a high incidence of *Orobanche* parasites comprising growing in said geographical area an *Orobanche* resistant tomato plant according to any of the preceding embodiments.

29. A method of controlling parasitic plants of the Orobanchaceae family, particularly *O. aegyptiaca*, in tomato crops, particularly in field grown tomato crops, comprising obtaining an *Orobanche* resistant tomato plant according to any of the preceding embodiments and growing said plant in a field contaminated with seeds of the *Orobanche* parasite.

30. A method of producing an *Orobanche* resistant tomato plant comprising grafting
    a) the scion of an *Orobanche* resistant tomato plant according to any one of embodiments 1-25 on the rootstock of a sensitive tomato plant, or
    b) the rootstock of an *Orobanche* resistant tomato plant according to any one of embodiments 1-25 on the scion of a sensitive tomato plant.

31. A tomato plant exhibiting a resistance to a parasitic plant of the genus *Orobanche* obtainable by a method according to any one of embodiments 27, 28 and 31.

32. Fruit of a tomato plant according to any one of embodiments 1 to 25 and 31.

33. A fruit according to embodiment 32 which is a processed fruit.

34. Use of the seed deposited under accession number NCIMB 41586 for the production of an *Orobanche* resistant tomato plant.

The invention claimed is:

1. A tomato cultivar exhibiting resistance to a parasitic plant of the genus *Orobanche*, wherein said resistance is controlled by a genetic determinant, said genetic determinant is represented by a single gene which shows a recessive inheritance, wherein said genetic determinant is obtained from tomato line ORT-10, deposited with NCIMB under accession number NCIMB 41586, further wherein said genetic determinant is in a homozygous state in said cultivar.

2. The tomato cultivar of claim 1, wherein said genetic determinant controls inhibition of a chemical stimulant that causes germination of seeds of a parasitic plant of the genus *Orobanche*.

3. The tomato cultivar of claim 1, which provides a root exudate which upon application to seeds of a parasitic plant of the genus *Orobanche*, leads to a germination rate in a seed germination assay of not more than 5%.

4. The tomato cultivar of claim 1, which provides a root extract upon extraction of root tissue with ethyl acetate, which upon application to seeds of a parasitic plant of the genus *Orobanche*, leads to a germination rate in a seed germination assay of not more than 5%.

5. The tomato cultivar according to claim 1, wherein said cultivar is resistant to at least one parasite selected from the group consisting of *Orobanche aegyptiaca, O. ramosa, O. crenata, O. cernua*, particularly *O. aegyptiaca*.

6. The tomato cultivar according to claim 1, wherein said cultivar is obtained from a donor plant comprising a genetic determinant controlling expression of the *Orobanche* resistance phenotype, tomato line ORT-10, deposited with NCIMB under accession number NCIMB 41586, through steps of (a) introgression of said genetic determinant into a recipient plant, which is susceptible to infestations with the *Orobanche* parasite, to obtain F1 plants, (b) self fertilization of said F1 plants to obtain F2 plants, and optionally (c) backcrossing of said F2 plants with said tomato line ORT-10.

7. The tomato cultivar according to claim 1, wherein said cultivar is selected from the group consisting of an inbred, a hybrid and a male sterile tomato cultivar, further wherein said resistance becomes manifest in the behavior of the cultivar towards an infestation with an *Orobanche* parasite, in that the resistant cultivar is only affected by a decrease of less than 5%, in one or more of the parameters selected from the group consisting of plant height, wet and dry weight of the root system, wet and dry weight of the foliage, dry and wet weight of the infested root including the broomrape parasite.

8. The tomato cultivar according to claim 1, which cultivar is a lycopene enriched tomato plant, with a lycopene content in the range of between 40 mg/kg and 200 mg/kg, or more.

9. A hybrid tomato plant providing *Orobanche* resistance produced by crossing tomato plant line ORT-10, seeds of which were deposited with NCIMB under accession number NCIMB 41586, as a parent with another tomato plant line.

10. A method of producing an *Orobanche* resistant tomato cultivar comprising the steps of introgressing from a donor plant of tomato line ORT-10, deposited with NCIMB under accession number NCIMB 41586, comprising a genetic determinant directing or controlling expression of the *Orobanche* resistance phenotype into a recipient plant, which is susceptible to infections with the *Orobanche* parasite, by (a) crossing said donor plant with said recipient plant to obtain F1 progeny plants, (b) self fertilization of said F1 plants to obtain F2 progeny plants and/or backcrossing said F1 plants with said tomato line ORT-10 to obtain a progeny plant exhibiting the *Orobanche* resistance, and (c) screening for and selecting from the progeny plants a plant exhibiting an *Orobanche* resistant phenotype and, optionally, harvesting the resultant progeny seed.

11. The method according to claim 10, wherein the genetic determinant directing or controlling expression of the *Orobanche* resistance phenotype is introgressed into a recipient tomato line which contains a high content of carotenoids, selected from the group consisting of lycopene, lutein, phytoene, phytofluene, neurosporene, alpha-carotene, beta-carotene, [gamma]-carotene, [zeta]-carotene, astaxanthine, and zeaxanthin.

12. The method according to claim 11, wherein content of lycopene is in the range of between 40 mg/kg and 200 mg/kg, or more.

13. The method according to claim 10, wherein the genetic determinant directing or controlling expression of the *Orobanche* resistance phenotype is introgressed into a recipient tomato line which has one or more of the processing quality factor (PQF) traits selected from the group consisting of:
    a. Holding ability of the fruit on the plant characteristics selected from the group consisting of firm fruit walls and thick skin, no decay of older fruits, no germination of seeds in the older fruits, no breakdown of sugars inside the older fruits, and no fermentation within the older fruit;
    b. Firmness of the fruits to withstand mechanical harvesting and transportation as well as storage under open sky conditions at 38° C. without significant breakdown and disease development;
    c. Firmness of the fruits to withstand high pressure steam of 15 to 30 psi at 105° to 120° to −120° C. and/or application of chemicals to peel the skin off the fruits;
    d. Firmness of the fruits to withstand high pressure steam for cooking as whole tomatoes;

e. Firmness of the fruits to withstand cutting to make diced tomato products; and f. Firmness of the sliced and diced tomato products to withstand cooking with high pressure steam.

14. A method for securing tomato fruit production to a commercially relevant extent in a geographical area with a high incidence of *Orobanche* parasites comprising growing in said geographical area the *Orobanche* resistant tomato cultivar according to claim 1.

15. A method of controlling parasitic plants of the Orobanchaceae family, in field grown tomato crops, comprising obtaining the *Orobanche* resistant tomato cultivar according to claim 1 and growing said cultivar in a field contaminated with seeds of the *Orobanche* parasite.

16. A method of producing an *Orobanche* resistant tomato cultivar comprising grafting
   a) the scion of the *Orobanche* resistant tomato cultivar according to claim 1 on the rootstock of a tomato plant sensitive to *Orobanche* infestations, or
   b) the rootstock of a second *Orobanche* resistant tomato cultivar according to claim 1 on the scion of a tomato plant sensitive to *Orobanche* infestations.

17. Fruit or a processed fruit of the tomato cultivar according to claim 1.

18. A method of producing carotenoids selected from the group consisting of lycopene, lutein, phytoene, phytofluene, neurosporene, alpha-carotene, beta-carotene, [gamma]-carotene, [zeta]-carotene, astaxanthine, and zeaxanthin and precursors thereof, comprising the steps of:
   a) providing the *Orobanche* resistant tomato cultivar according to claim 1;
   b) growing the tomato cultivar to full maturity of the tomato fruit;
   c) harvesting the fruits, and
   d) extracting said carotenoids from the fruit.

19. A method for the manufacture of vegetal extract or concentrate that is enriched in carotenoid and/or phytosterol comprising the steps of:
   a) providing the *Orobanche* resistant tomato cultivar according to claim 1;
   b) growing the tomato cultivar to full maturity of the tomato fruit;
   c) harvesting the fruits, and
   d) extracting said carotenoids from the fruit.

* * * * *